(12) United States Patent
Kawaguchi et al.

(10) Patent No.: US 9,084,878 B2
(45) Date of Patent: Jul. 21, 2015

(54) ULTRASOUND TREATMENT INSTRUMENT

(71) Applicant: OLYMPUS MEDICAL SYSTEMS CORP., Tokyo (JP)

(72) Inventors: Yuki Kawaguchi, Hachioji (JP); Tomoyuki Tsuchiya, Fuchu (JP); Satoshi Homma, Hino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 13/897,810

(22) Filed: May 20, 2013

(65) Prior Publication Data

US 2013/0303949 A1  Nov. 14, 2013

Related U.S. Application Data

(63) Continuation of application No. PCT/JP2012/077784, filed on Oct. 26, 2012.

(60) Provisional application No. 61/551,676, filed on Oct. 26, 2011.

(51) Int. Cl.
*A61N 7/00* (2006.01)
*A61B 17/28* (2006.01)
(Continued)

(52) U.S. Cl.
CPC ............... *A61N 7/00* (2013.01); *A61B 17/282* (2013.01); *A61B 17/320092* (2013.01);
(Continued)

(58) Field of Classification Search
CPC ............ A61B 17/282; A61B 2017/2825; A61B 17/320092; A61B 18/1442; A61B 18/1445; A61B 2019/304; A61N 7/00

USPC ............................................................. 601/2
See application file for complete search history.

(56) References Cited

U.S. PATENT DOCUMENTS 5,507,773 A   4/1996  Huitema et al.
5,873,873 A   2/1999  Smith et al.
(Continued)

FOREIGN PATENT DOCUMENTS

EP   0 800 792 A1   10/1997
EP   0 897 696 A1   2/1999
(Continued)

OTHER PUBLICATIONS

International Search Report issued in International Patent Application No. PCT/JP2012/077784 dated Nov. 27, 2012.
Mar. 13, 12015 Office Action issued in European Patent Application No. 12844337.1.

*Primary Examiner* — Long V Le
*Assistant Examiner* — Colin T Sakamoto
(74) *Attorney, Agent, or Firm* — Oliff PLC

(57) ABSTRACT

With respect to a forceps type treatment instrument including an ultrasound probe that protrudes from a treatment instrument main body at a position separated to a distal end side from a shaft portion, and a jaw that is displaceable between a closed state and an opened state by being linked with swing action of an clamp arm in a position separated to a distal end side from the shaft portion, stoppers are extendedly provided toward a clamp arm side from a treatment instrument main body side in a state in which edge portions at a distal end side are set to located at a distal end side from a locus of a proximal end of the jaw, and entry of a living body into a gap of the treatment instrument main body and the clamp arm is restricted.

3 Claims, 15 Drawing Sheets

(51) Int. Cl.
*A61B 17/32* (2006.01)
*A61B 19/00* (2006.01)
*A61B 18/14* (2006.01)

(52) U.S. Cl.
CPC ........ *A61B 18/1442* (2013.01); *A61B 18/1445* (2013.01); *A61B 2017/2825* (2013.01); *A61B 2017/320072* (2013.01); *A61B 2019/304* (2013.01); *A61B 2019/481* (2013.01)

(56) References Cited

U.S. PATENT DOCUMENTS

| | | | |
|---|---|---|---|
| 6,280,407 | B1 | 8/2001 | Manna et al. |
| 7,563,269 | B2 * | 7/2009 | Hashiguchi ................... 606/169 |
| 8,025,630 | B2 * | 9/2011 | Murakami et al. ................ 601/2 |
| 2005/0033324 | A1 * | 2/2005 | Phan .............................. 606/148 |
| 2007/0191713 | A1 * | 8/2007 | Eichmann et al. ............ 600/471 |
| 2010/0063525 | A1 | 3/2010 | Beaupre et al. |
| 2010/0331873 | A1 | 12/2010 | Dannaher et al. |

FOREIGN PATENT DOCUMENTS

| | | |
|---|---|---|
| EP | 0 908 153 A1 | 4/1999 |
| JP | A-8-33628 | 2/1996 |
| JP | A-11-104142 | 4/1999 |
| JP | A-11-192235 | 7/1999 |
| JP | A-2001-37771 | 2/2001 |
| JP | A-2004-209042 | 7/2004 |
| JP | 2005-253674 | 9/2005 |
| JP | A-2009-514566 | 4/2009 |
| WO | WO 98/14126 A1 | 4/1998 |
| WO | WO 2007/047380 A2 | 4/2007 |

* cited by examiner

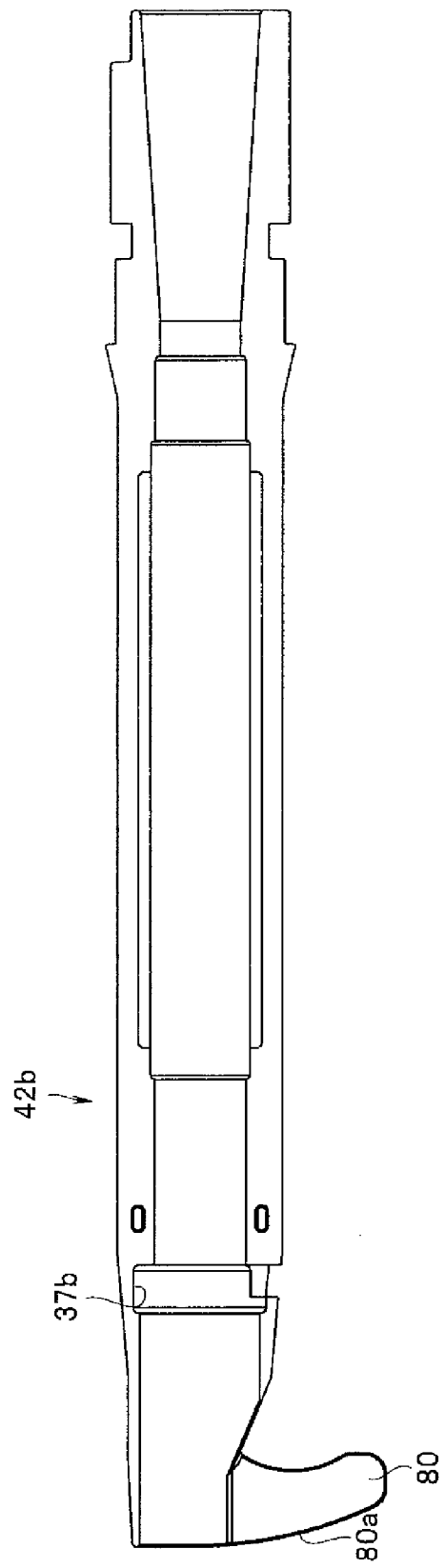

ULTRASOUND TREATMENT INSTRUMENT

CROSS REFERENCE TO RELATED APPLICATION

This application is a continuation application of PCT/JP2012/077784 filed on Oct. 26, 2012 and claims benefit of U.S. Provisional Patent Application No. 61/551,676 filed in the U.S.A. on Oct. 26, 2011, the entire contents of which are incorporated herein by this reference.

BACKGROUND OF THE INVENTION

1. Field of the Invention

The present invention relates to an ultrasound treatment instrument that performs treatment such as dissection, ablation, or coagulation of living tissue by using ultrasound.

2. Description of the Related Art

Conventionally, as a treatment instrument for performing surgical treatment, an ultrasound treatment instrument has been known. An ultrasound treatment instrument is capable of performing treatment such as dissection, ablation, or coagulation of living tissue, for example, by transmitting ultrasound vibration to the living tissue, or merging ultrasound vibration and a high-frequency current and transmitting the ultrasound vibration and the high-frequency current.

In particular, as an ultrasound treatment instrument favorable for fine and delicate surgical treatment such as thyroidectomy, among ultrasound treatment instruments, a forceps type (scissors type) ultrasound treatment instrument is disclosed in for example, Japanese Patent Application Laid-Open Publication No. 2009-514566. The forceps type ultrasound treatment instrument has a treatment instrument main body (handle assembly) containing a waveguide (transmission rod) that transmits ultrasound vibration to a distal end side from a proximal end side, and a clamp arm that is pivotally supported swingably at the treatment instrument main body via a shaft portion. From a distal end of the treatment instrument main body, an ultrasound probe (blade) that is a distal end portion of the waveguide is protruded. A bent portion for avoiding interference with the treatment instrument main body is provided at a distal end side of the clamp arm that intersects the treatment instrument main body via the shaft portion. A jaw (clamp member) for sandwiching living tissue between the jaw and the ultrasound probe is provided at a distal end side from the bent portion. Further, the jaw is provided with a pad formed from a resin or the like, in a region contactable with the ultrasound probe.

SUMMARY OF THE INVENTION

An ultrasound treatment instrument according to one aspect of the present invention includes a treatment instrument main body, a clamp arm that is pivotally supported swingably at the treatment instrument main body via a shaft portion, an ultrasound probe that protrudes from the treatment instrument main body in a position separated to a distal end side from the shaft portion, a base that is provided at the clamp arm in a position separated to a distal end side from the shaft portion, and displaces between a closed state being in close proximity to the ultrasound probe and an opened state separated from the ultrasound probe by being linked with a swing action of the clamp arm, a jaw that is supported swingably around an axis extending in a width direction of the base to extend in a longitudinal direction of the base, and has a proximal end portion located at a proximal end side from the distal end portion of the base to form a space between the proximal end portion and the base, stoppers that are provided toward side portions of the jaw from the treatment instrument main body, and restrict entry of a living body into a gap of the treatment instrument main body and the clamp arm between the proximal end portion of the jaw and the shaft portion, and operation portions that cause the treatment instrument main body and the clamp arm to move relatively from a closed state to an opened state so that edge portions at distal end sides of the stoppers are located at a distal end side from the proximal end portion of the jaw.

BRIEF DESCRIPTION OF THE DRAWINGS

FIG. 24 is a plan view showing the sheath member.

DETAILED DESCRIPTION OF THE PREFERRED EMBODIMENTS

Figure 1:
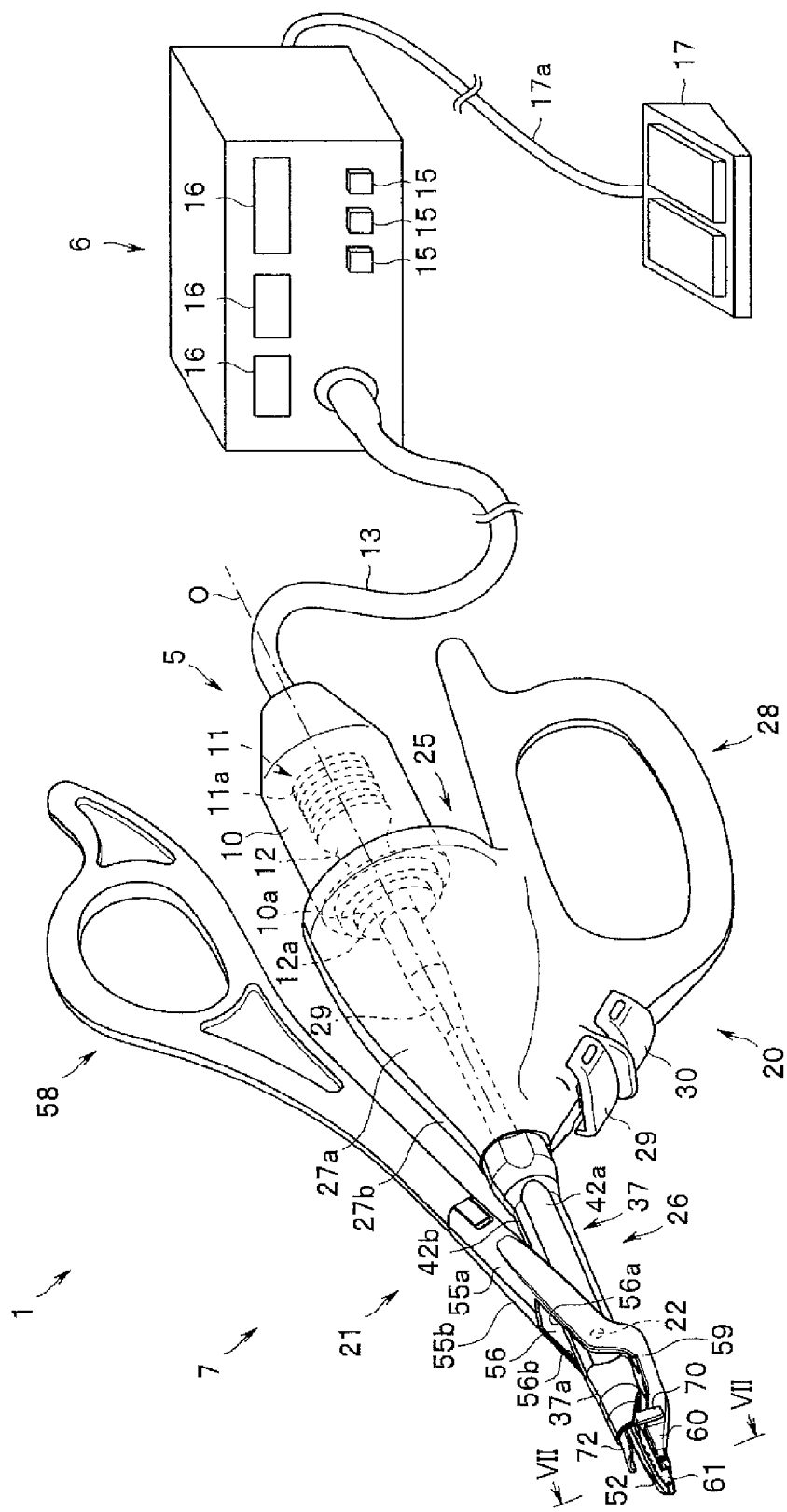
FIG. 1 is a configurational view of an ultrasound surgery apparatus.

As shown in FIG. 1, an ultrasound surgical apparatus 1 that is a medical apparatus according to a first embodiment of the present invention is configured by including an ultrasound transducer 5, an output control apparatus 6 to which the ultrasound transducer 5 is connected, and a treatment instrument 7 that functions as an ultrasound treatment instrument by having a distal end portion of the ultrasound transducer 5 connected thereto.

The ultrasound transducer 5 has an ultrasound transducer 11 contained in a transducer cover 10 that is formed into a substantially cylindrical shape. In the present embodiment, the ultrasound transducer 11 is configured by, for example, a plurality of piezoelectric elements 11a each formed into a ring shape being arranged in a long axis direction of the transducer cover 10. Further, a proximal end portion of a horn 12 that performs amplitude expansion of ultrasound vibration is connected to a distal end portion of the ultrasound transducer 11. A distal end portion 12a of the horn 12 is protruded to an outside via a connector portion 10a that is formed at a distal end portion of the transducer cover.

A cable 13 is extended from a proximal end portion of the transducer cover 10, and the ultrasound transducer 5 is connected to the output control apparatus 6 via the cable 13.

A mode for supplying at least any one of a drive signal for ultrasound output and a drive signal for high-frequency current output to the ultrasound transducer 5 is set in the output control apparatus 6. More specifically, three output modes that are, for example, an ultrasound output mode, a high-frequency current output mode and a simultaneous output mode of ultrasound and high-frequency current are set in the output control apparatus 6. In order to perform selection or the like of the output modes, various operation buttons 15 are placed on the output control apparatus 6. Further, display apparatuses 16 for displaying a selection state of the output mode, various output values and the like are placed on the output control apparatus 6. Output setting of the respective modes can be performed in a touch panel manner on the display apparatuses 16. Alternatively, setting can be changed with buttons not illustrated. Further, a foot switch 17 for turning on or off the output of a drive signal corresponding to the output mode is connected to the output control apparatus 6 via a cable 17a.

The treatment instrument 7 is configured by a forceps type (scissors type) treatment instrument having a treatment instrument main body 20 containing a waveguide 51 (see FIG. 3) that transmits ultrasound vibration to a distal end side from a proximal end side, and a clamp arm 21 that is pivotally supported swingably (rotatably) at the treatment instrument main body 20 via a shaft portion 22.

Figure 2:
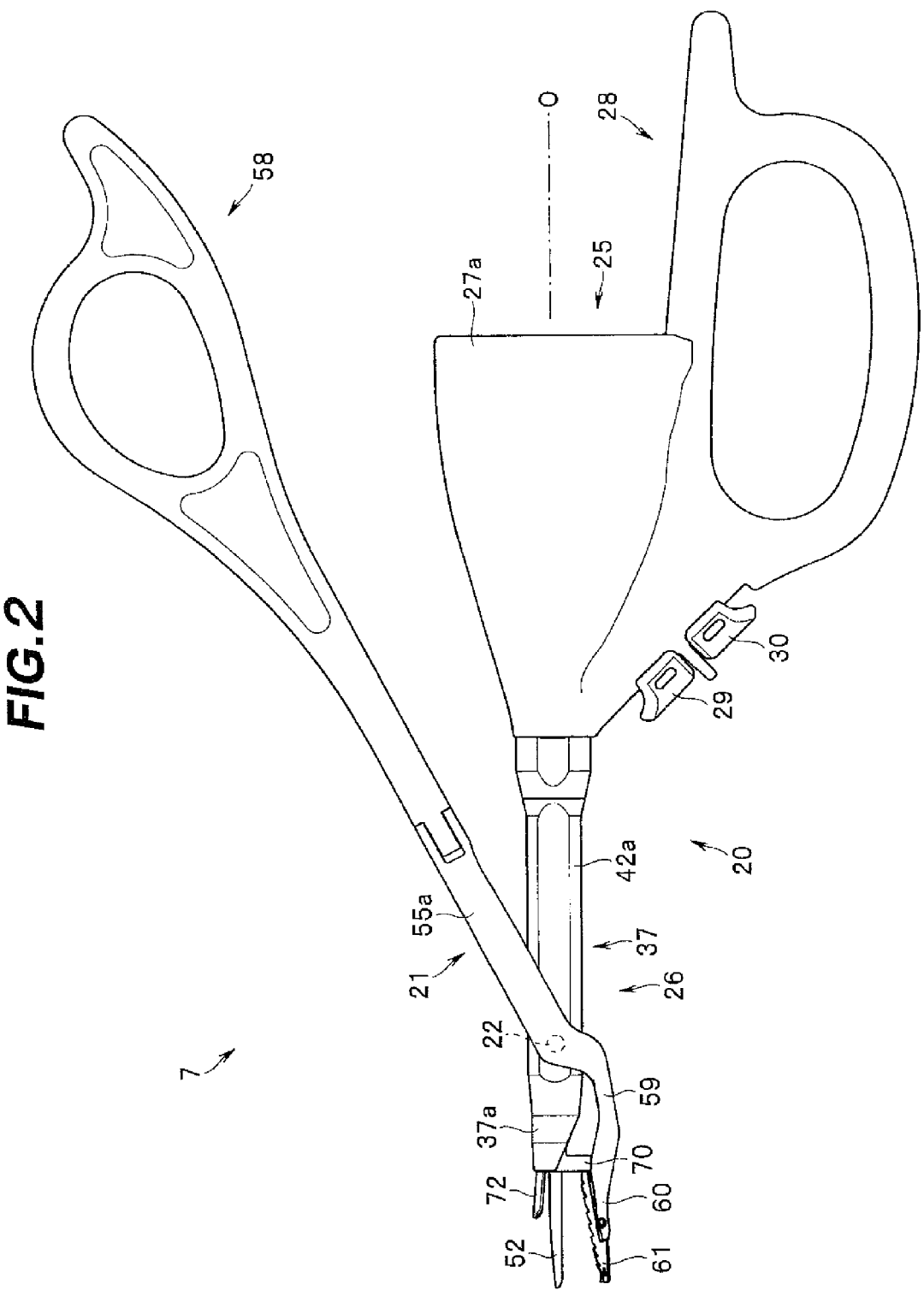
FIG. 2 is a side view of an ultrasound treatment instrument.
Figure 3:
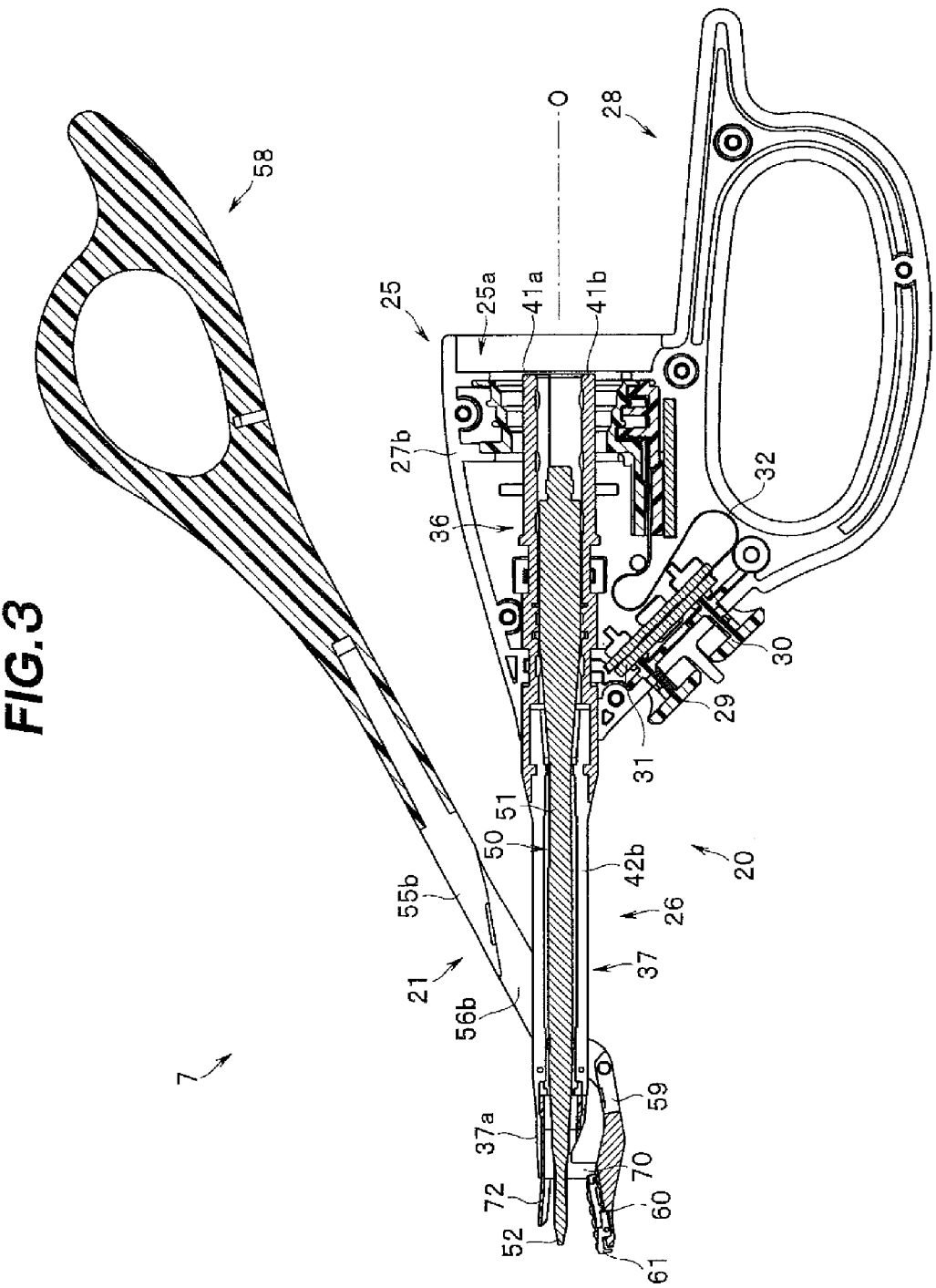
FIG. 3 is a vertical sectional view of the ultrasound treatment instrument.

For example, as shown in FIGS. 2 and 3, the treatment instrument main body 20 is configured by having a housing 25 formed into a substantially conical shape, and a sheath 26 held by the housing 25.

The housing 25 is configured by, for example, housing members 27a and 27b composed of a pair of resin molded products laterally divided being joined to each other by snap-fitting, press-fitting, bonding, adhesion, welding or mechanical means. A connector receiving portion 25a for detachably connecting the connector portion 10a of the ultrasound transducer 5 is opened, in a proximal end portion of the housing 25.

Further, in a proximal portion side of the housing 25, a first finger rest portion 28 formed into a ring shape is integrally formed in a position that is offset from a center axis O of the housing 25.

Further, two switch buttons 29 and 30 are provided on a front edge portion of the first finger rest portion 28. The switch buttons 29 and 30 are placed at a position to which a forefinger (and a middle finger) of a surgeon or the like is faced in a state in which the surgeon or the like inserts the middle finger and a ring finger, or the ring finger and a fifth finger into the first finger rest portion 28, for example. The switch button 29 is a switch button for turning on or off output of the drive signal corresponding to an output mode, for example. The switch button 30 is a switch for changing an output value of the ultrasound vibration or the high-frequency current, for example. As shown in FIG. 3, proximal portions of the switch buttons 29 and 30 are provided connectively to a control board 31 placed in the housing 25. Further, a flexible board 32 is provided extendedly from the control board 31, and the flexible board 32 is connected to the connector receiving portion 25a. Thereby, operation signals to the switch buttons 29 and 30 are transmitted to the output control apparatus 6 via the connector receiving portion 25a. Subsequently, the operation signals are transmitted to the output control apparatus 6, and thereby the surgeon or the like also can perform an on/off operation of output of the drive signal at a hand side without operating the foot switch 17 or the like.

The sheath 26 is configured by having a first sheath 36 that is mainly inserted through an inside of the housing 25, and a second sheath 37 that is connected to a distal end portion of the first sheath 36 and extends to an outside of the housing 25.

The first sheath 36 is configured by, for example, a substantially cylindrical member formed by a pair of sheath members 41a and 41b that are vertically divided being joined to each other by snap-fitting, press-fitting, bonding, adhesion, welding or mechanical means. Further, the second sheath 37 is configured by, for example, a substantially cylindrical member formed by a pair of sheath members 42a and 42b that are laterally divided being joined to each other by snap-fitting, press-fitting, boning, adhesion, welding or mechanical means. The first and the second sheaths 36 and 37 are connected by, for example, an outer periphery of a proximal end portion of the second sheath 37 being fitted onto an inner periphery of the distal end portion of the first sheath 36, and configure the long continuous sheath 26. Inside the sheath 26, the waveguide 51 formed from a conductive metal is held via an elastic member (not illustrated) such as a rubber ring or a plastic member, or a flange formed by a diameter of a part of the waveguide being enlarged.

In the housing 25, a proximal end portion of the sheath 26 (that is, a proximal end portion of the first sheath 36) is faced to an inside of the connector receiving portion 25a. The distal end portion 12a of the horn 12 that protrudes from the connector portion 10a is inserted into the proximal end portion of the first sheath 36 when the connector portion 10a of the ultrasound transducer 5 is connected to the connector receiving portion 25a. Here, the distal end portion 12a of the horn 12 is connectable to a proximal end portion of the waveguide 51 by screwing or the like, and by the connection, the horn 12 and the waveguide 51 are connected acoustically and electrically. Thereby, ultrasound vibration that is generated in the ultrasound transducer 11 of the ultrasound transducer 5 is transmitted to the waveguide 51, and a high-frequency current (drive signal) outputted from the output control apparatus 6 is transmitted to the waveguide 51.

At a distal end portion of the sheath 26 (that is, the distal end portion of the second sheath 37), a taper portion 37a in which an outer diameter is reduced is formed. From a distal end of the taper portion 37a, an ultrasound probe 52 provided at a distal end portion of the waveguide 51 is protruded. Note that in the present embodiment, the ultrasound probe 52 is formed integrally with the waveguide 51 from a conductive metal, and a continuous probe unit 50 is configured by the waveguide 51 and the ultrasound probe 52.

The ultrasound probe 52 is bent into substantially a shape of a letter "J". In the present embodiment, the ultrasound probe 52 has a function as a first electrode section that transmits a high-frequency current to living tissue, besides a function of transmitting ultrasound vibration to living tissue.

Figure 4:
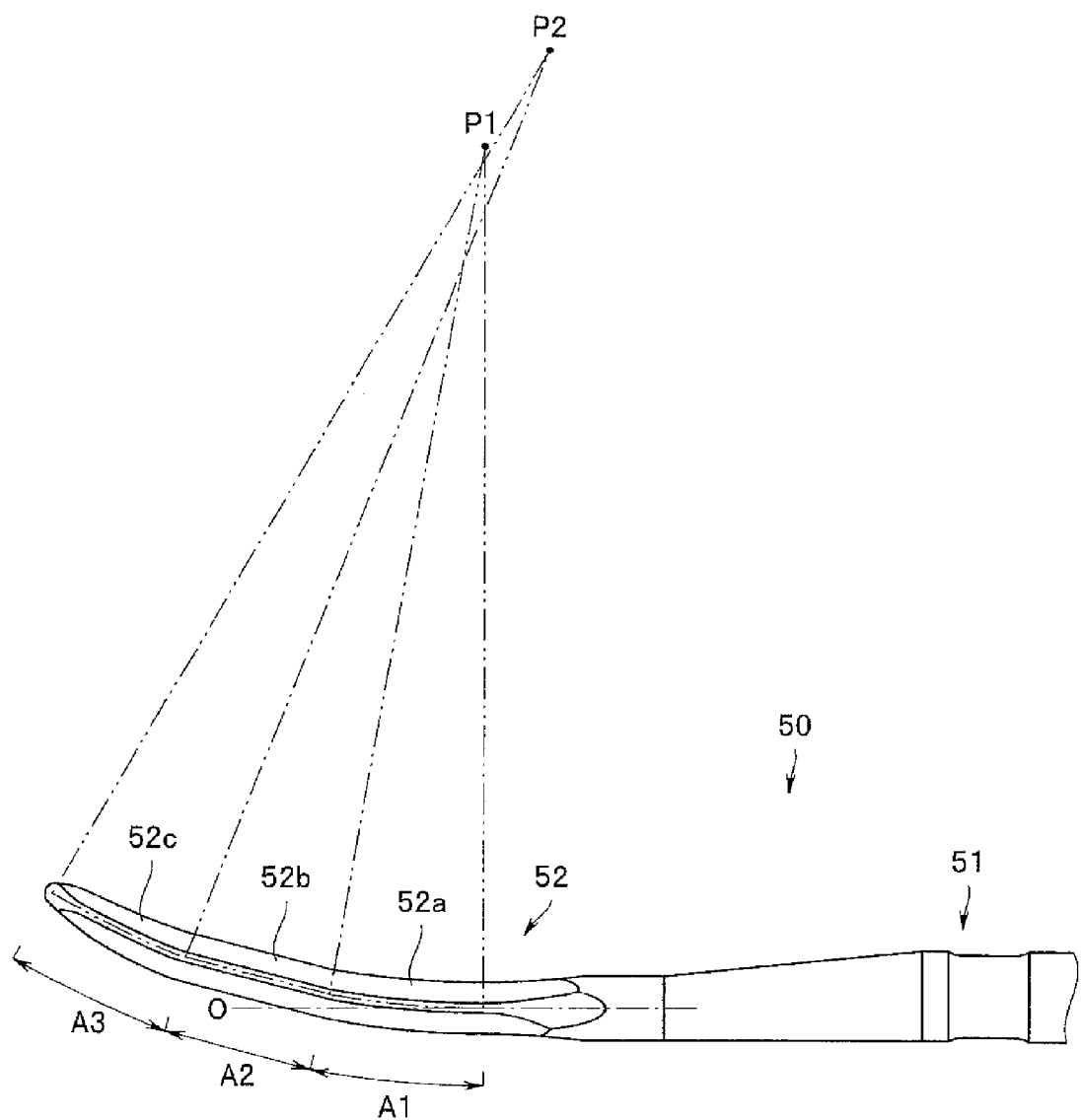
FIG. 4 is a plan view showing an opposing surface to a jaw, of an ultrasound probe.

Here, as a shape of the ultrasound probe 52, an entire region from a proximal end portion to a distal end portion can be formed by being bent along a single curved line, but in order to secure a region in which a size is controlled with high precision in at least a part of the ultrasound probe 52, the ultrasound probe 52 is configured by having a straight-line region halfway therein. Namely, in view of the fact that working precision on the occasion of work of a straight-line shape being performed is more excellent than working precision on the occasion of work of a bent shape being performed, the straight-line region is formed halfway in the ultrasound probe 52. For example, as shown in FIG. 4, the ultrasound probe 52 of the present embodiment is configured by having a first bent region 52a that is formed in a region A1, a straight-line region 52b that is formed in a region A2 continuing to the first bent region 52a, and a second bent region 52c that is formed in a region A3 at a distal end side and continues to the straight-line region 52b. Furthermore, in order to allow a degree of freedom of design with respect to the bent shape as the entire ultrasound probe 52, the first bent region 52a and the second bent region 52c are formed along curved lines with different curvatures. However, the first bent region 52a and the second bent region 52c may be formed along curved lines with the same curvature.

The clamp arm 21 is configured by a rod-shaped member formed by a pair of arm members 55a and 55b that are laterally divided being joined to each other by snap-fitting, press-fitting, bonding, adhesion, welding, press-fitting or mechanical means. Concave portions 56a and 56b that face each other are provided halfway in the arm members 55a and 55b, and by the concave portions 56a and 56b, an opening 56 that extends in a longitudinal direction of the clamp arm 21 is formed halfway in the clamp arm 21. A distal end side of the sheath 26 is inserted through the opening 56, and an inner surface side of the opening 56 and an outer surface side of the sheath 26 are connected via the shaft portion 22, whereby the clamp arm 21 is pivotally supported swingably (rotatably) with respect to the treatment instrument main body 20.

A second finger rest portion 58 that is paired with the first finger rest portion 28 that is provided at the treatment instrument main body 20 is connectively provided at a proximal end portion of the clamp arm 21. The second finger rest portion 58 is configured by a ring shape that is favorable for insertion of a thumb of a surgeon or the like being formed, for example. For example, the surgeon or the like causes the finger inserted into the first finger rest portion 28 (for example, the ring finger and the fifth finger) and the finger inserted into the second finger rest portion 58 (for example, the thumb) to act relatively, and thereby the clamp arm 21 is caused to act swingably with the shaft portion 22 as the support point.

A bent portion 59 for avoiding interference with the sheath 26 when the clamp arm 21 is caused to act swingably is provided, at a distal end side of the clamp arm 21 that intersects the treatment instrument main body 20 via the shaft portion 22. Further, a base 60 facing the ultrasound probe 52 is provided at a distal end side of the bent portion 59. The base 60 is provided with a jaw 61 formed from a conductive metal.

Figure 6:
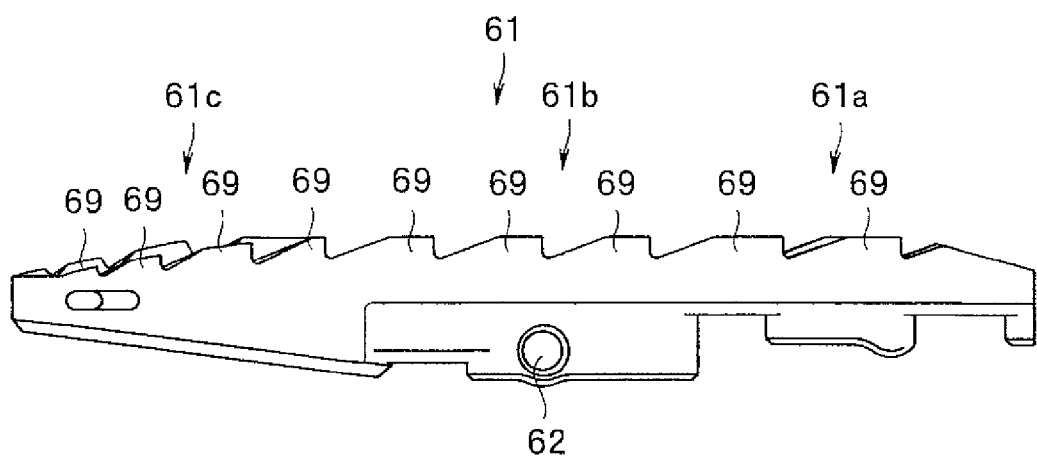
FIG. 6 is a side view of the jaw.

When description is made more specifically, the jaw 61 has a pin hole 62 that penetrates therethrough in a width direction, for example, as shown in FIG. 6, and is held by the base 60 via a pin 60a that is inserted through the pin hole 62 (see FIG. 8 to FIG. 13). Namely, the jaw 61 is held in a swingable state within a predetermined range with the pin 60a as a center, with respect to the base 60. Thereby, the jaw 61 is displaceable between a closed state in which the jaw 61 contacts the ultrasound probe 52, and an opened state in which the jaw 61 separates from the ultrasound probe 52 by being linked with swing of the clamp arm 21. Note that the jaw 61 has a function as a second electrode section in correspondence with the ultrasound probe 52 that functions as the first electrode section. Note that a shape of the jaw is not limited to the illustrated example as a matter of course.

A region where the jaw 61 and the ultrasound probe 52 displace to be contactable and separable (openable and closable) configures a treatment section 63 that is an effective region for performing various kinds of treatment such as dissection, ablation, and coagulation on living tissue. A region from a proximal end portion of the jaw 61 to the shaft portion 22 is a treatment incapable region 64 which is incapable of performing various kinds of treatment on living tissue.

Figure 5:
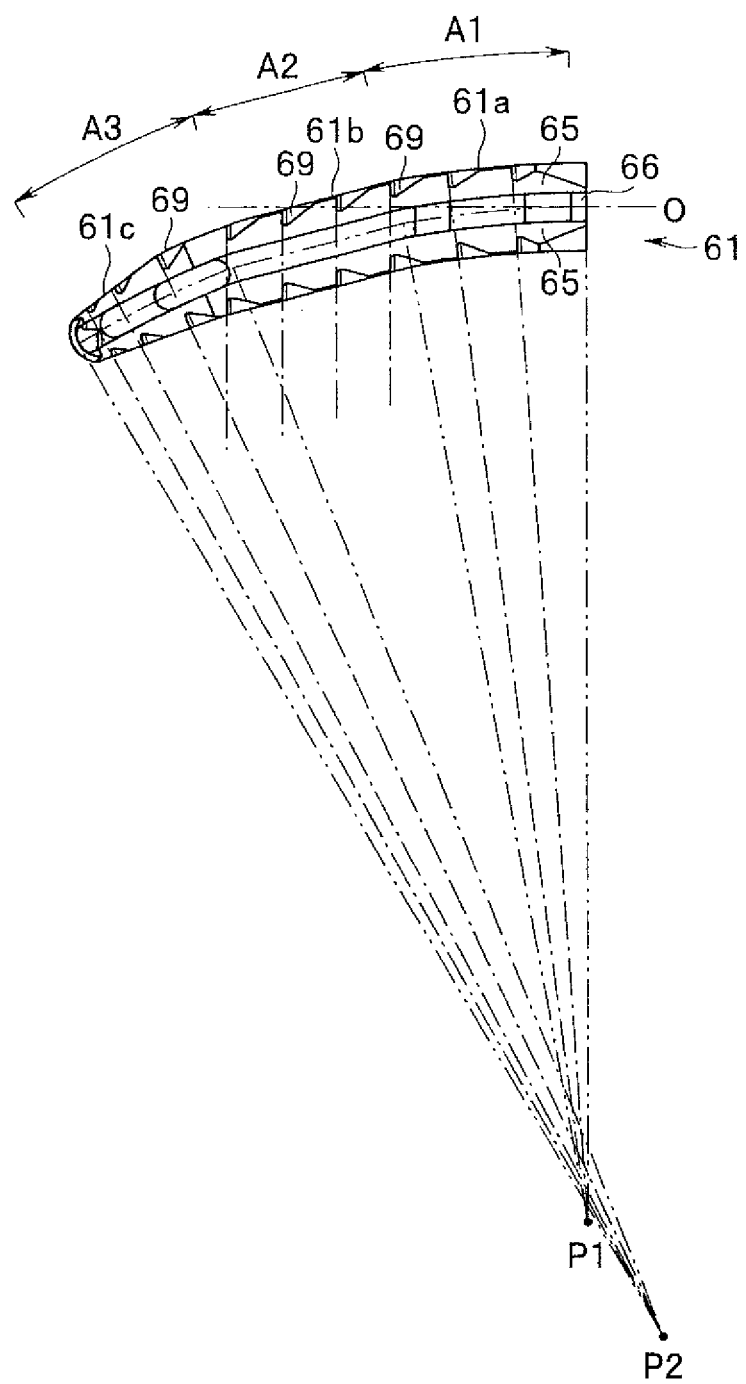
FIG. 5 is a plan view showing an opposing surface to the ultrasound probe, of the jaw.

Here, the jaw 61 is bent into substantially the shape of a letter "J" which is symmetrical with the ultrasound probe 52, as shown in FIG. 5, for example. Namely, the jaw 61 is configured by having a first bent region 61a formed in a region A1 at a proximal portion side, a straight-line region 61b formed in a region A2 continuing to the first bent region 61a, and a second bent region 61c formed in a region A3 at a distal end side continuing to the straight-line region 61b, similarly to the ultrasound probe 52. Further, in order to allow the degree of freedom in design for the bent shape as the entire jaw 61, the first bent region 61a and the second bent region 61c are formed along curved lines with different curvatures. However, the first bent region 61a and the second bent region 61c may be formed along curved lines with the same curvature.

Figure 7:
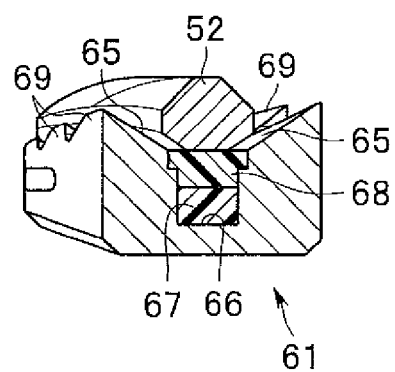
FIG. 7 is a sectional view taken along the VII-VII line of FIG. 1.

Further, for example, as shown in FIG. 7, in the jaw 61, inclined surfaces 65 that are inclined at predetermined depression angles toward a central portion from respective side edge portions are formed on an opposing surface to the ultrasound probe 52. Further, in the jaw 61, a concave groove 66 that extends in a longitudinal direction is provided on a bottom portion of the inclined surface 65 that is the opposing surface to the ultrasound probe 52. In the concave groove 66, a heat insulating member 67 of a resin, for example, is provided. Further, in the concave groove 66, a pad 68 formed from a resin material such as Teflon (registered trade name), for example, is provided on a top layer of the heat insulating member 67. The pad 68 has a surface exposed from the concave groove 66 set as a contact surface with the ultrasound probe 52.

Further, for example, as shown in FIGS. 5 and 6, teeth 69 for slip proof each formed into a shape of a sawtooth are formed at the respective side edge portions of the jaw 61 by cutting or the like. Here, if cutting of the respective teeth 69 is performed from the same direction to the jaw 61 that is formed into the bent shape, teeth heights of the respective teeth 69 become uneven. Therefore, in the present embodiment, in order to even out the teeth heights of the respective teeth 69 into a predetermined range, the respective teeth 69 are formed by cutting that differs for each of the regions 61a to 61e. Namely, for example, as shown by the dashed lines in FIG. 5, the respective teeth 69 formed in the first bent region 61a is formed by cutting being performed in a state in which a tool is set in a direction perpendicular to the first bent region 61a (perpendicular direction from a center point P1 of a circular arc). Further, the respective teeth 69 formed in the straight-line region 61b are formed by cutting being performed in a state in which the tool is set at a predetermined angle with respect to the straight-line region 61b. Further, the respective teeth 69 formed in the second bent region 61c are formed by cutting being performed in a state in which the tool is set in a direction perpendicular to the second bent region 61c (perpendicular direction from a center point P2 of a circular arc).

Figure 8:
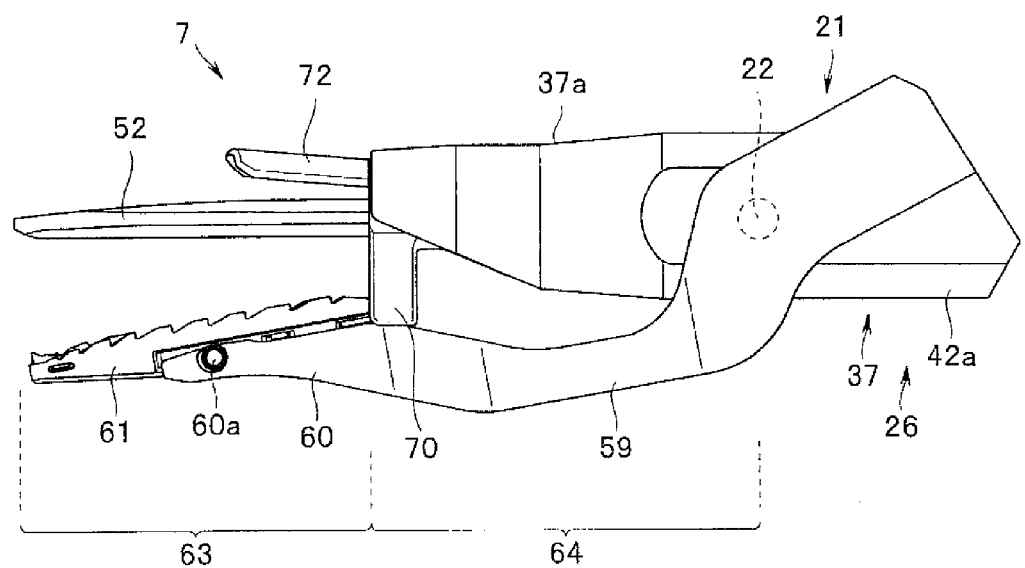
FIG. 8 is a side view showing a distal end portion of the ultrasound treatment instrument in a state in which a treatment section is opened.
Figure 9:
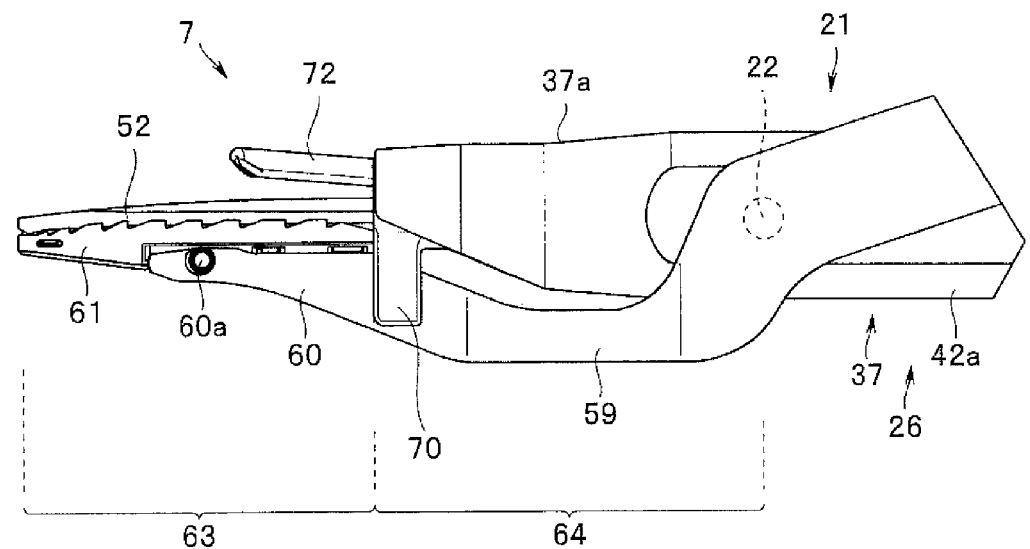
FIG. 9 is a side view showing a distal end portion of the ultrasound treatment instrument in a state in which the treatment section is closed.
Figure 10:
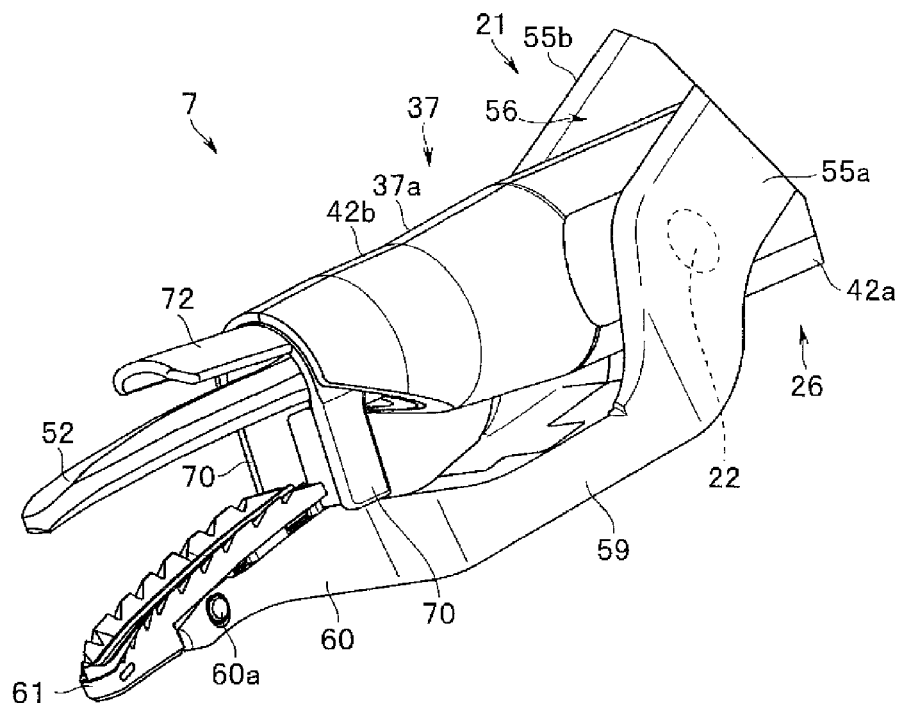
FIG. 10 is a perspective view of the distal end portion of the ultrasound treatment instrument in the state in which the treatment section is opened, seen from an ultrasound probe side.

In the treatment instrument 7 that is configured as above, plate-shaped stoppers 70 that extend to be directed to side portions of the clamp arm 21 from proximal end portion both sides of the ultrasound probe 52 and are each formed into a substantially rectangular shape in side view are provided at the distal end portion of the treatment instrument main body 20 (that is, the distal end portion of the second sheath 37), as shown in FIG. 8 to FIG. 13, for example. The stoppers 70 are for restricting entry of a living body to a gap of the second sheath 37 and the clamp arm 21 between the proximal end portion of the jaw 61 and the shaft portion 22. Namely, as shown in FIGS. 8 and 10, for example, when the jaw 61 is in an opened state, the stoppers 70 are extended from a proximal portion of the ultrasound probe 52 to a directly rear side of the jaw 61, and restricts entry of the living body into the treatment incapable region 64.

For example, as shown in FIGS. 11 and 14 to 16, the respective stoppers 70 are held by the sheath 26 via a cylindrical member 71 held in the second sheath 37.

Figure 11:
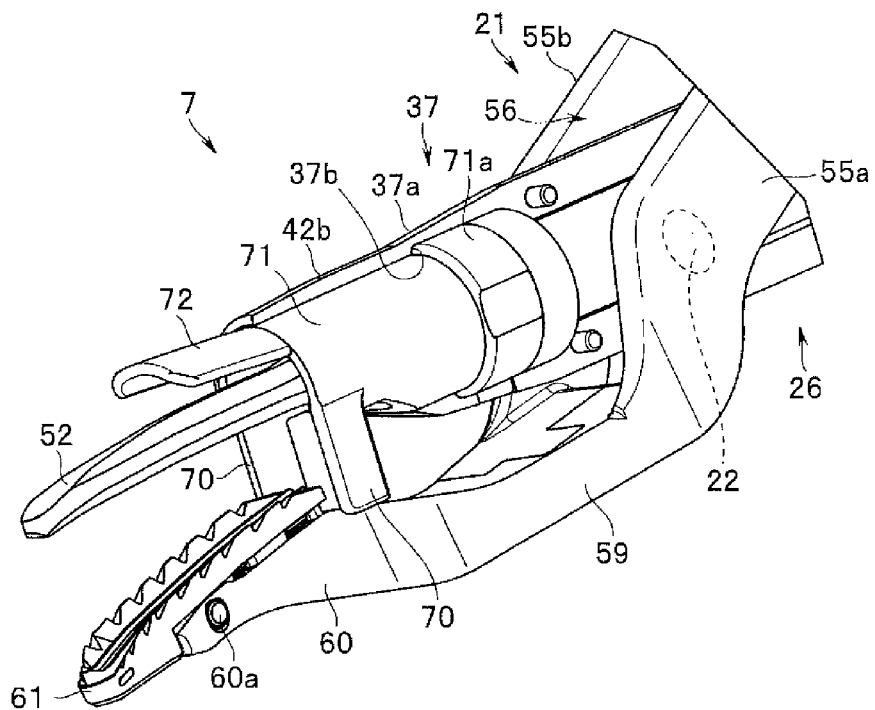
FIG. 11 is a perspective view showing the ultrasound treatment instrument of FIG. 10 in a state in which a part of a sheath member configuring a sheath is removed.

When description is made more specifically, a concave portion 37b for holding the cylindrical member 71 is formed on a distal end portion inner periphery of the second sheath 37, as shown in FIG. 11, for example. A proximal end portion of the cylindrical member 71 in a state in which the ultrasound probe 52 is inserted therethrough is held in the concave portion 37b. Namely, as illustrated, a step portion 71a is formed at the proximal end portion of the cylindrical member 71, and the step portion 71a is engaged in the concave portion 37b, whereby the cylindrical member 71 is prevented from dropping off from the second sheath 37. Further, a protruding portion 71b is formed at a proper place on the step portion 71a of the cylindrical member 71, and the protruding portion 71b is engaged in an inside of the concave portion 37b, whereby rotation of the cylindrical member 71 relative to the second sheath 37 is prevented.

Figure 12:
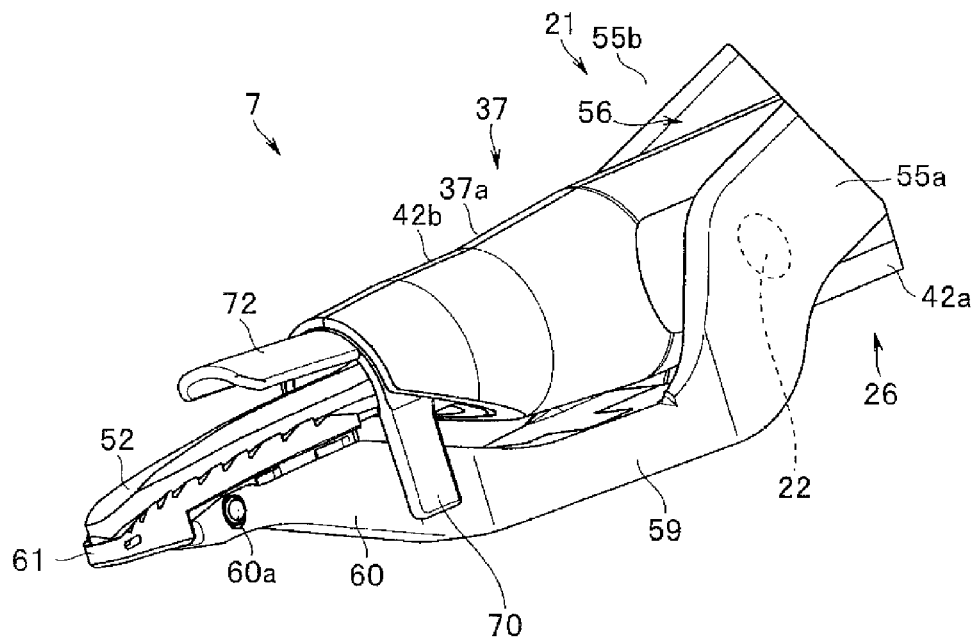
FIG. 12 is a perspective view of the distal end portion of the ultrasound treatment instrument in the state in which the treatment section is closed, seen from the ultrasound probe side.
Figure 13:
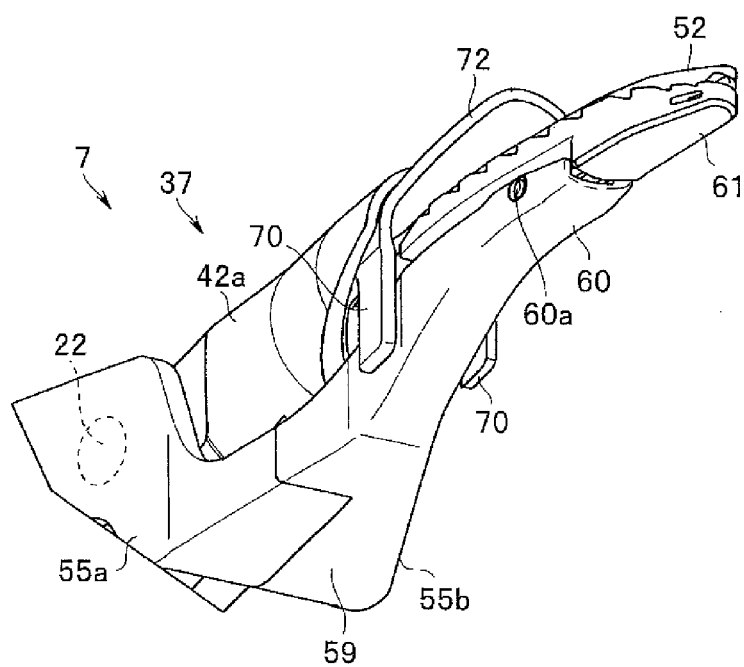
FIG. 13 is a perspective view of the distal end portion of the ultrasound treatment instrument in the state in which the treatment section is closed, seen from a jaw side.
Figure 14:
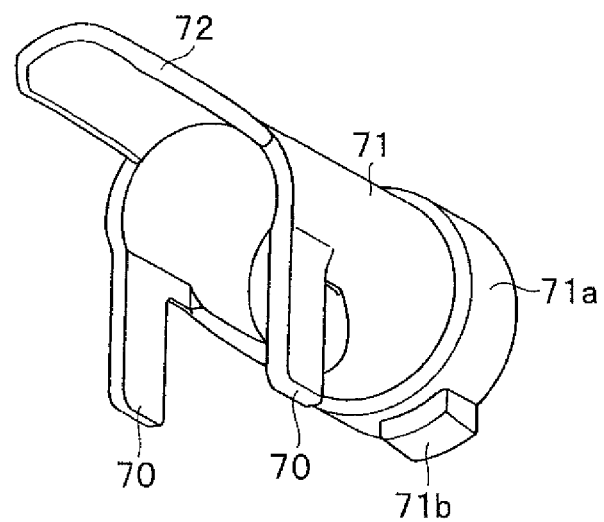
FIG. 14 is a perspective view of a stopper member.
Figure 15:
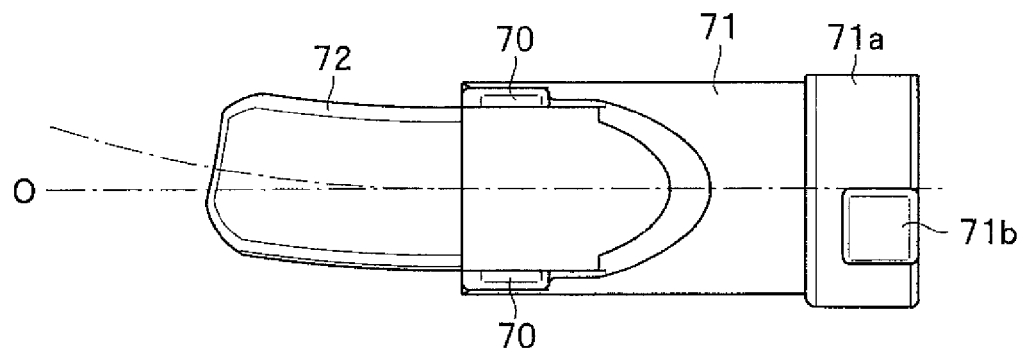
FIG. 15 is a plan view of the stopper member.
Figure 16:
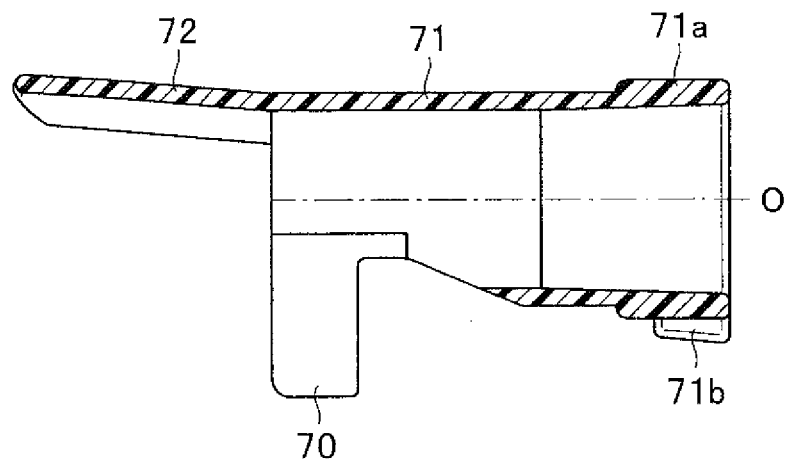
FIG. 16 is a sectional view taken along the XVI-XVI line of FIG. 15.

At both sides of the proximal end portion of the ultrasound probe 52, the respective stoppers 70 are linearly extended to be directed to the sides of the clamp arm 21 that are at a proximal end side of the jaw 61 from a distal end portion of the cylindrical member 71. In this case, the respective stoppers 70 are set so that edge portions at distal end sides thereof are always located at a distal end side with respect to a locus of movement of the proximal end portion of the jaw 61 following swing of the clamp arm 21. In other words, the respective stoppers 70 are set so as to be always superimposed from the sides onto the proximal end portion of the jaw 61 while the jaw 61 moves, for example, from the closed position shown in FIG. 9 to the opened position shown in FIG. 8 by swing of the clamp arm 21. Further, as shown in FIGS. 9, 12 and 13, for example, lengths of the respective stoppers 70 are each preferably set at a length within a range in which an extension end portion of the stopper 70 does not protrude from a back surface of the clamp arm 21 (that is, a surface on a side that does not face the treatment instrument main body 20, of the clamp arm 21) when the jaw 61 is in the closed state.

Further, clearances of the respective stoppers 70 with respect to the clamp arm 21 are desirably set to be as small as possible within a range without inhibiting swing of the clamp arm 21.

Further, from a distal end portion of the cylindrical member 71, a probe cover 72 that faces the ultrasound probe 52 is extendedly provided. The probe cover 72 is configured by a scoop-shaped member that is located at an opposite side from the jaw 61, and covers a predetermined range of the proximal portion side of the ultrasound probe 52. In the present embodiment, the probe cover 72 is bent to follow a bent shape of the ultrasound probe 52 (see, for example, FIG. 15), and is configured to cover the first bent region 52a in a position separated at a predetermined space from the ultrasound probe 52, for example. The range to be covered may be a whole of the ultrasound probe 52, or a partial region of the ultrasound probe 52.

When treatment on living tissue is performed with use of the treatment instrument 7 as above, a surgeon or the like causes the jaw 61 to perform opening and closing action with respect to the ultrasound probe 52 (that is, cause the treatment section 63 to perform opening and closing action) through operation to the first and the second finger rest portions 28 and 58 that are the operation portions, and sandwiches the living tissue between the ultrasound probe 52 and the pad 68 of the jaw 61. In the state, the surgeon or the like operates the foot switch 17, the switch button 29, or the like, and transmits at least any one of ultrasound vibration and a high-frequency current to the living tissue from the ultrasound probe 52. Thereby, treatment such as dissection, ablation, or coagulation is performed on the living tissue.

On the occasion, even when the jaw 61 is in the opened state with respect to the ultrasound probe 52 (even when the treatment section 63 is in the opened state), entry of the living tissue into the treatment incapable region 64 at the proximal portion side from the jaw 61 is restricted by the stoppers 70 that are across the rear side of the opened treatment section 63. Further, the stoppers 70 are set so that the edge portions at the distal end sides thereof are located at the distal end side from the locus of the proximal end of the jaw 61 following displacement of the base 60, and thereby simultaneously restrict entry of the living tissue into a gap between the base 60 and the proximal end portion of the jaw 61. Thereby, the treatment instrument 7 can sandwich the living tissue by only the treatment section 63 between the ultrasound probe 52 and the jaw 61. Accordingly, the surgeon or the like can perform quick and appropriate treatment on the living tissue by the treatment section 63, and can immediately recognize completion when the treatment is completed. Namely, transmission of an erroneous sense that the treatment is still continuing to the hand of the surgeon even after completion of the treatment on the living tissue by the treatment section 63 by the living tissue being sandwiched in the treatment incapable region 64 can be appropriately prevented. Accordingly, the surgeon or the like can immediately stop the output of the ultrasound vibration or the like after the treatment on the living tissue is completed, prevents the pad 68 from being excessively worn by the ultrasound vibration or the like, and can realize extension of the life of the pad 68. Thereby, the malfunction of the metallic portions of the probe 52 and the jaw 61 directly contacting each other or the like can be avoided.

In this case, in particular, the edge portion at the distal end side of the stopper 70 is set to be located at the distal end side from the locus of movement of the proximal end of the jaw 61, and thereby, the function of restricting entry of the living tissue into the treatment incapable region 64, and the function of restricting entry of a living body into the gap between the base 60 and the proximal end portion of the jaw 61 can be simultaneously realized by the simple configuration in which only the stoppers 70 are provided.

Further, the clearances with respect to the side portions of the clamp arm 21, of the respective stoppers 70 are properly set, whereby the respective stoppers 70 can be also caused to function as guide members on the occasion of the clamp arm 21 swinging, and the malfunction of the jaw 61 being offset in the lateral direction with respect to the ultrasound probe 52 on the occasion of sandwiching living tissue or the like can be eliminated. Namely, in order to cause the clamp arm 21 to swing smoothly with respect to the treatment instrument main body 20, a predetermined play needs to be given to the shaft portion 22, and when such a play is given, occurrence of backlash or the like on the occasion of swing of the clamp arm 21 can be suppressed by the respective stoppers 70 being caused to function as the guide members.

Further, the lengths of the stoppers 70 are each set at the length within the range in which the extension end portion does not protrude from the back surface side of the clamp arm 21 when the jaw 61 is in the closed state, and thereby, reduction in operability can be prevented even when the stoppers 70 are provided at the treatment instrument 7. However, when priority is given to prevention of entry of tissue into the non-treatment region, when the opening amount between the jaw and the probe is made large, the design of the extension end portion to protrude from the back surface side of the clamp arm 21 may be made.

Further, the straight-line regions 52b and 61b are provided halfway in the ultrasound probe 52 and the jaw 61, and thereby, the regions in which sufficient size control is performed for the clearance or the like of the ultrasound probe 52 and the inclined surfaces 65 of the jaw 61 can be formed, halfway in the treatment section 63 which forms a bent shape as a whole. Living tissue such as a blood vessel is sandwiched in the straight-line regions 52b and 61b in which sufficient size control is performed like this, and thereby treatment such as blood vessel sealing can be realized stably.

Further, the heat insulating member 67 is caused to lie on a lower layer of the pad 68 placed in the concave groove 66 that is formed in the jaw 61, and thereby the heat generated in the pad 68 by ultrasound vibration can be prevented from being directly transmitted to the back surface side of the jaw 61.

Further, the proximal portion side of the ultrasound probe 52 is covered with the probe cover 72, and thereby even in the case of the surgeon or the like performing treatment with attention focused on the distal end side of the ultrasound probe 52 or the like, unintentional contact of the proximal portion side of the ultrasound probe 52 with the temperature raised by the ultrasound vibration and living tissue can be avoided. In this case, the probe cover 72 is integrally formed on the cylindrical member 71 that holds the stoppers 70, and thereby the probe cover 72 can be configured by a simple configuration without increase of the number of components. Further, for example, if the probe cover 72 is provided restrictively to correspond to the first bent region 52a, interference of the probe cover 72 with living tissue can be avoided at the time of treatment such as blood vessel sealing with use of the straight-line region 52b. However, the range that is covered may be the whole of the ultrasound probe 52 or a partial region of the ultrasound probe 52.

Further, on the occasion of formation of the teeth 69 for slip proof at the respective side edge portions of the jaw 61, the tool is set in the directions perpendicular respectively to the circular arcs of the respective bent regions 61a and 61c at the time of cutting for the first and the second bent regions 61a and 61c, and thereby, the teeth heights of the respective teeth 69 can be evened out.

Figure 17:
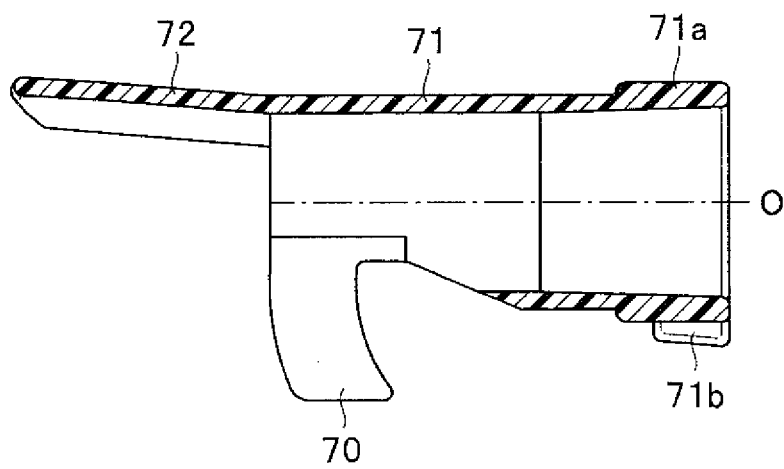
FIG. 17 is a sectional view showing a modification of the stopper member.

Note that in the aforementioned embodiment, various modifications and changes can be made. For example, in the aforementioned embodiment, one example in which the stoppers 70 are extendedly provided linearly to be directed to the sides of the clamp arm 21 from the sides of the ultrasound probe 52 is described, but the present invention is not limited thereto, and, for example, as shown in FIG. 17, the stoppers 70 also can be each extendedly provided in the circular-arc shape.

Figure 18:
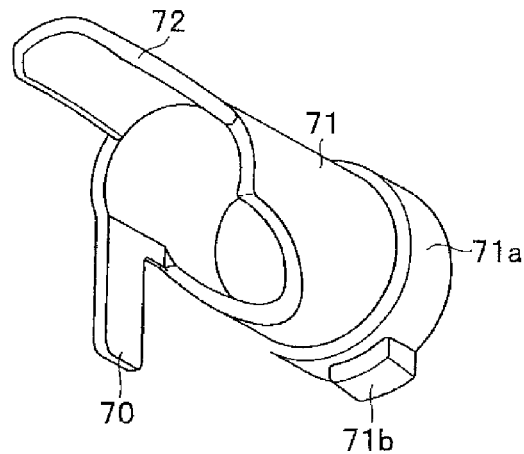
FIG. 18 is a perspective view showing the modification of the stopper member.

Further, in the aforementioned embodiment, one example in which the pair of stoppers 70 are placed at both the sides of the ultrasound probe 52 is described, but the present invention is not limited to this, and, for example, as shown in FIG. 18, the stopper 70 also can be provided at only one side of the ultrasound probe.

Figure 19:
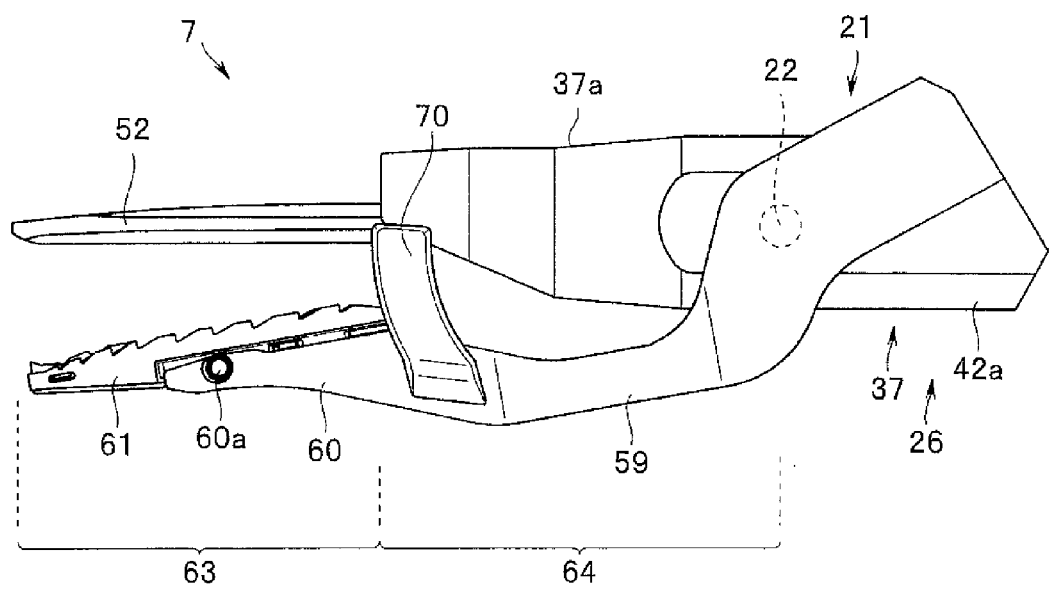
FIG. 19 is a side view showing a modification of the distal end portion of the ultrasound treatment instrument.
Figure 20:
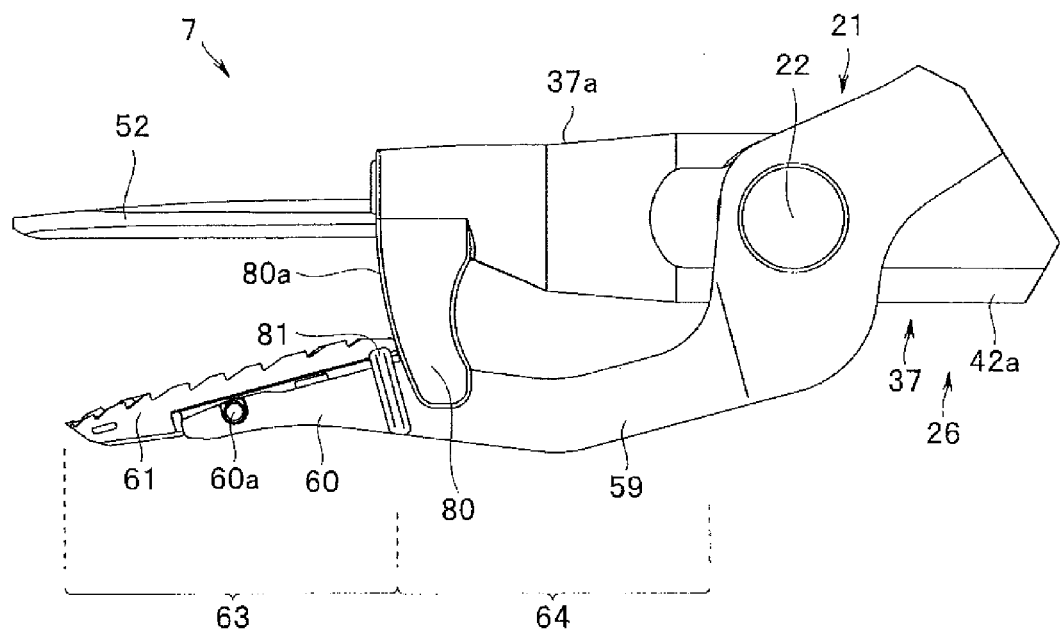
FIG. 20 is a side view showing the distal end portion of the ultrasound treatment instrument in the state in which the treatment section is opened.
Figure 21:
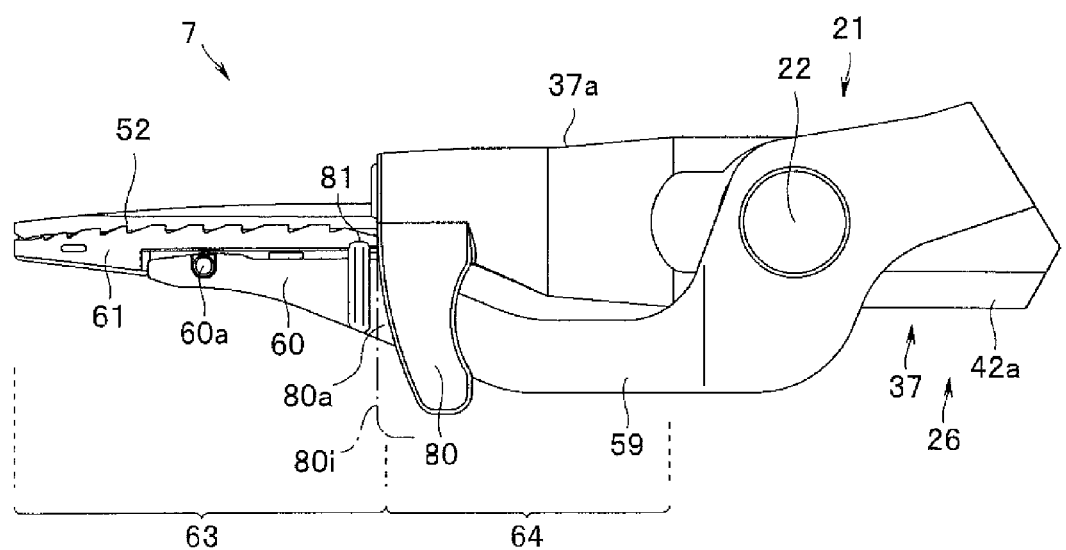
FIG. 21 is a side view showing the distal end portion of the ultrasound treatment instrument in the state in which the treatment section is closed.

Further, in the aforementioned embodiment, one example in which the stoppers 70 are extendedly provided to be directed to the clamp arm 21 side from the treatment instrument main body 20 side is described, but the present invention is not limited thereto, and, for example, as shown in FIG. 19, the stoppers 70 also can be extendedly provided to be directed to the treatment instrument main body 20 side from the clamp arm 21 side.

Next, with reference to FIG. 20 to FIG. 24, a second embodiment of the present invention will be described. Note that the present embodiment mainly differs from the aforementioned first embodiment in the point in which the configuration of the stopper is changed, the point in which auxiliary stoppers are provided at a base side, and the point in which the probe cover is abolished. Besides, the same components as in the aforementioned first embodiment will be assigned with the same reference signs and the description thereof will be omitted.

As shown in FIG. 20 to FIG. 24, respective stoppers 80 of the present embodiment are configured by metallic members integrally formed at distal end portions of respective left and right sheath members 42a and 42b that configure the second sheath 37. The stoppers 80 are formed integrally with the sheath members 42a and 42b and made of a metal like this, and thereby as compared with the case of the stoppers being configured by a resin or the like, rigidity of the respective stoppers 80 is enhanced.

The respective stoppers 80 are each formed by being bent into a circular-arc shape, and are more specifically formed into a circular-arc shape with the shaft portion 22 that pivotally supports the clamp arm 21 at the treatment instrument main body 20 in the present embodiment. Thereby, as compared with, for example, the case in which the stoppers are extendedly provided linearly (virtually expressed by the dashed line by being assigned with reference sign 80i in FIG. 21), the extension end portions of the stoppers 80 can be offset to the proximal end side of the treatment instrument 7. Accordingly, even when the lengths of the respective stoppers 80 are set to be long so as to cause the respective stoppers 80 to function effectively even in a state in which the jaw 61 is opened to a relatively large opening degree with respect to the ultrasound probe 52, for example, the stoppers 80 can be restrained from hindering treatment. Namely, even when the stoppers 80 are set to be long so that the extension end portions of the stoppers 80 protrude from back surface of the clamp arm 21 (that is, a surface at the side that does not face the treatment instrument main body 20 of the clamp arm 21), the extension end portions of the protruded stoppers 80 are offset to the proximal end side from the treatment section 63, and therefore, the extension end portions of the stoppers 80 can be prevented from interfering with living tissue or the like. In addition, when the stoppers 80 are bent, the extension end portions of the stoppers 80 can be caused to be close to the shaft portion 22 side as compared with the case in which the stoppers are each formed into a straight-line shape, and therefore, even when the stoppers are caused to function with respect to the same opening degree of the probe 61, the entry preventing function for living tissue can be realized with shorter extension lengths.

Figure 22:
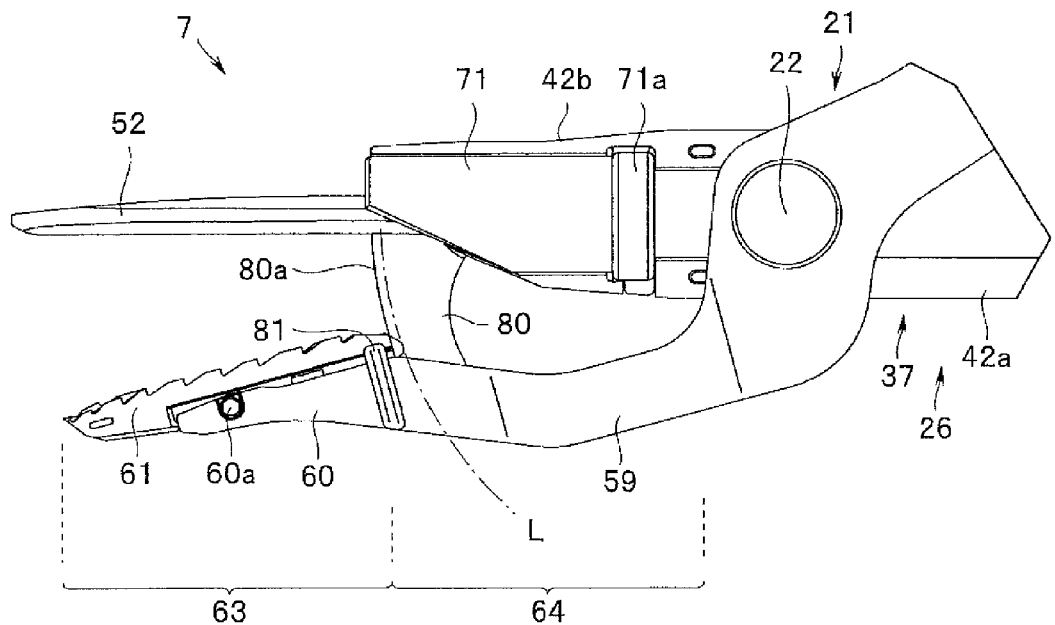
FIG. 22 is a side view showing the distal end portion of the ultrasound treatment instrument in a state in which a part of the sheath member configuring the sheath is removed.

Further, for example, as shown in FIG. 22, an edge portion 80a at a distal end side of the stopper 80 is set to be located at a distal end side from a locus L of the proximal end of the jaw 61 following the movement of the base 60. Thereby, the respective stoppers 80 are set to be always superimposed onto the proximal end portion of the jaw 61 from the sides while the jaw 61 moves from a closed position shown in FIG. 21, for example, to an opened position shown in FIG. 20 by swing of the clamp arm 21. Accordingly, by the simple configuration in which only the stoppers 80 are provided, the function of restricting entry of living tissue into the treatment incapable region 64, and the function of restricting entry of a living body into a gap between the base 60 and the proximal end portion of the jaw 61 can be simultaneously realized.

Figure 23:
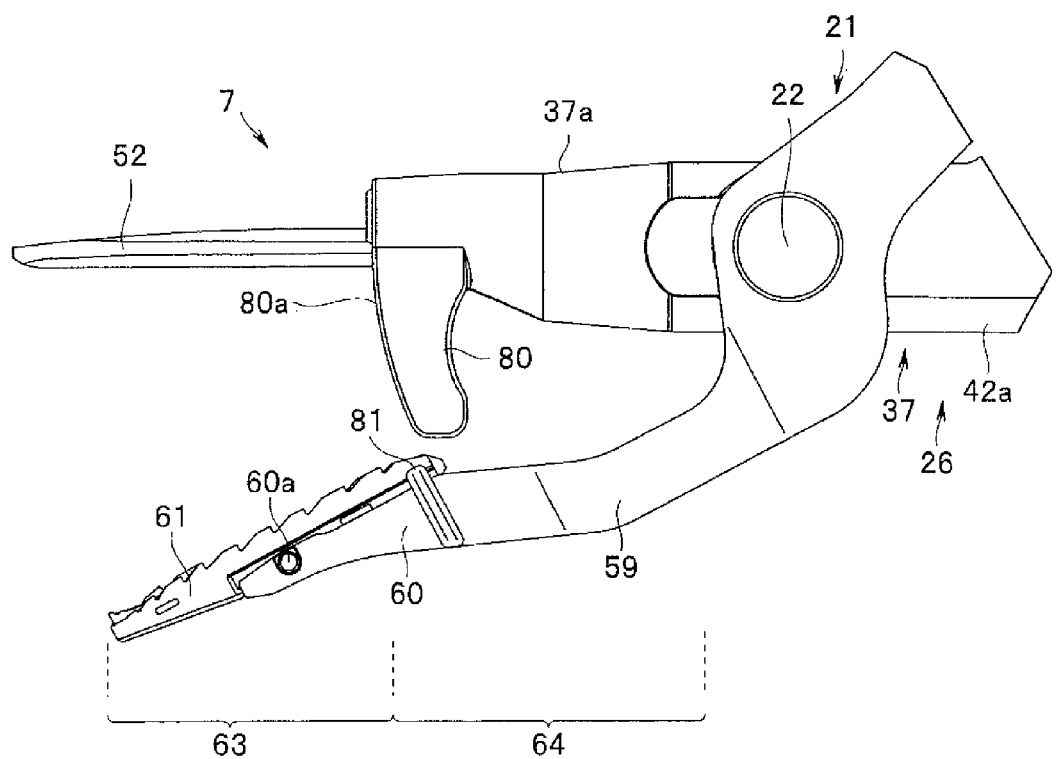
FIG. 23 is a side view showing the distal end portion of the ultrasound treatment instrument in a state in which the treatment section is opened to a fully opened position.

Further, auxiliary stoppers 81 that face side portions at the proximal end side of the jaw 61 are provided protrudingly from the base 60 of the present embodiment. In the present embodiment, the auxiliary stopper 81 is provided at a position adjacent to the stopper 80 in a distal end side from the stopper 80 in order to prevent interference with the stopper 80. Further, a height of the auxiliary stopper 81 is set to be higher than the gap from the base 60 at the proximal end side of the jaw 61 and lower than the jaw 61. By providing the auxiliary stopper 81 like this, even when the jaw 61 is opened to a vicinity of a fully opened position that is not assumed in normal use, and the extension step portion of the stopper 80 is located at the probe 52 side from the jaw 61 as shown in FIG. 23, for example, living tissue can be prevented from entering the gap between the base 60 and the proximal end side of the jaw 61.

Note that the present invention is not limited to the respective embodiments described above, and various modifications and changes can be made. Such various modifications and changes are also within the technical range of the present invention. For example, the configurations described in the aforementioned respective embodiments, and the respective modifications thereof and the like may be properly combined as a matter of course.

What is claimed is:

1. An ultrasound treatment instrument, comprising:
an ultrasound probe that transmits ultrasound vibration;
a treatment portion provided at a distal end side of the ultrasound probe for treating a subject by the ultrasound vibration;
a sheath through which the ultrasound probe is inserted;
a clamp arm that is pivotally supported swingably at the sheath via a shaft portion;
a base that is provided at the clamp arm in a position separated to a distal end side from the shaft portion;
a jaw that is supported swingably around an axis extending in a width direction of the base to extend in a longitudinal direction of the base, and has a proximal end portion located at a proximal end side from the distal end portion of the base to form a space between the proximal end portion and the base;
operation portions for operating the jaw to move between a closed state in which the jaw is in close proximity to the treatment portion and an opened state in which the jaw is separated from the treatment portion;
a stopper that protrudes from the sheath and extends towards a side portion of the jaw, and formed to be arranged at the side portion of the jaw and at a side portion of the base to cover the space when the jaw is moved from the opened state to the closed state; and
an auxiliary stopper that is provided protrudingly from the base to cover the space and to face a side portion of a proximal end side of the jaw.

2. The ultrasound treatment instrument according to claim 1, wherein the auxiliary stopper is provided protrudingly from the base to be adjacent to the stopper and to face the side portion of the proximal end side of the jaw.

3. The ultrasound treatment instrument according to claim 2, wherein the auxiliary stopper is provided protrudingly from the base to be adjacent to a distal end side of the stopper.

\* \* \* \* \*